United States Patent
Guo

(10) Patent No.: US 7,592,179 B2
(45) Date of Patent: Sep. 22, 2009

(54) FIVE-PART DIFFERENTIAL WHITE BLOOD CELL CONTROL AND METHOD FOR PREPARATION OF THE SAME

(75) Inventor: Xiaonan Guo, Shenzhen (CN)

(73) Assignee: Shenzhen Mindray Bio-Medical Electronic Co., Ltd. (CN)

( * ) Notice: Subject to any disclaimer, the term of this patent is extended or adjusted under 35 U.S.C. 154(b) by 0 days.

(21) Appl. No.: 11/872,481

(22) Filed: Oct. 15, 2007

(65) Prior Publication Data

US 2008/0293144 A1    Nov. 27, 2008

(30) Foreign Application Priority Data

May 25, 2007    (CN) .................. 2007 1 0106645

(51) Int. Cl.
*G01N 33/48* (2006.01)
*G01N 33/96* (2006.01)

(52) U.S. Cl. ................. 436/10; 436/8; 436/16; 436/17; 436/18; 436/63; 436/164; 436/166; 436/174; 436/175; 436/176; 435/2

(58) Field of Classification Search .......... 436/8, 436/10, 16, 17, 18, 63, 128, 164, 166, 174, 436/175, 176; 435/2
See application file for complete search history.

(56) References Cited

U.S. PATENT DOCUMENTS

| | | | |
|---|---|---|---|
| 5,262,327 A | 11/1993 | Ryan | |
| 5,270,208 A | 12/1993 | Ryan | |
| 5,320,964 A * | 6/1994 | Young et al. | 436/10 |
| 5,512,485 A | 4/1996 | Young et al. | |
| 5,516,695 A * | 5/1996 | Kim et al. | 436/17 |
| 5,639,630 A * | 6/1997 | Malin et al. | 435/28 |
| 5,672,474 A | 9/1997 | Ryan | |
| 5,677,145 A | 10/1997 | Ryan | |
| 5,731,205 A | 3/1998 | Ryan | |
| 5,840,515 A * | 11/1998 | Provost | 435/29 |
| 5,858,790 A | 1/1999 | Kim et al. | |
| 5,981,282 A * | 11/1999 | Ryan | 436/10 |
| 6,146,901 A * | 11/2000 | Carver et al. | 436/174 |
| 6,187,590 B1 | 2/2001 | Kim et al. | |
| 6,200,500 B1 | 3/2001 | Ryan | |
| 6,221,668 B1 | 4/2001 | Ryan et al. | |
| 6,399,388 B1 | 6/2002 | Ryan et al. | |
| 6,403,377 B1 * | 6/2002 | Ryan et al. | 436/8 |
| 6,406,915 B2 | 6/2002 | Ryan et al. | |
| 6,514,763 B2 | 2/2003 | Carver et al. | |
| 6,653,137 B2 | 11/2003 | Ryan | |
| 6,759,246 B1 | 7/2004 | Collins | |
| 6,762,055 B2 * | 7/2004 | Carver et al. | 436/10 |

OTHER PUBLICATIONS

China patent application No. 200710106645.3, Search Report dated Jul. 16, 2007.

* cited by examiner

*Primary Examiner*—Maureen M Wallenhorst
(74) *Attorney, Agent, or Firm*—Vista IP Law Group, LLP.

(57) ABSTRACT

The present invention provides a method for preparing a five-part differential white blood cell control and a white blood cell control prepared thereby. The white blood cell control obtained by the method of the present invention perfectly retains the light scattering properties of every type of white blood cells and has much higher stability than that of real white blood cells, and therefore can be used for the quality control of five-part differential hematology analyzers based on the principle of multi-angle light scattering.

16 Claims, 3 Drawing Sheets

DIFF

BASO

DIFF

BASO

DIFF

BASO

DIFF

BASO

US 7,592,179 B2

FIVE-PART DIFFERENTIAL WHITE BLOOD CELL CONTROL AND METHOD FOR PREPARATION OF THE SAME

STATEMENT OF RELEVANT APPLICATION

The present application claims the priority of China Patent Application No. CN200710106645.3 entitled "Five-part differential white blood cell control and method for preparation of the same", filed on May 25, 2007.

TECHNICAL FIELD

The present invention generally relates to hematology reference control, in particular to a method for preparing a white blood cell control and a white blood cell control prepared thereby.

BACKGROUND OF INVENTION

Hematology reference control, as a liquid comprising single or multi-component blood cells or blood cell analogs, which is as detectable as blood, is used for routinely monitoring the accuracy and precision of hematology analyzers. Along with the continuing development of hematology analyzers, the accompanying controls should also solve the problems of increased parameters, for example, the development of three-part differential white blood cell control to five-part differential white blood cell control or controls with more parameters. Compared with three-part differential hematology analyzers, five-part differential hematology analyzers make more use of electrical, optical, chemical staining characteristics or the like of white blood cells to achieve five-part differential detection of white blood cells. As different types of five-part differential hematology analyzers vary in principles of detection and the corresponding accompanying white blood cell controls also rely on varying principles, emphasis is more placed on "tailor-making". As is mentioned in U.S. Pat. No. 6,762,055, an accompanying control used in a certain type of hematology analyzer quite probably may not work efficiently in another type.

Attempts have been made to simulate five-part differential white blood cell controls using pollen, latex particles, various organic materials and fixed red blood cells. The methods of the prior art for preparing five-part differential white blood cell analogs can be summarized as follows: 1) treating animal red blood cells for simulation; and 2) treating mammal white blood cells (generally human white blood cells) for simulation.

When animal red blood cells are used for simulating five-part differential white blood cell components, the requirements for cell characteristics expand from the simple parameter of volume size to the characteristics such as conductivity, light scattering and cell chemical staining. Therefore, animal red blood cells should be subjected to proper treatment. For example, as is mentioned in U.S. Pat. Nos. 5,320,964 and 5,512,485, white blood cell analogs are comprised of red blood cells capable of simulating at least two kinds of physical properties of human white blood cells. Monocytes, lymphocytes and neutrophils are simulated by treating reptile red blood cells through a certain method as using a hypotonic solution containing an aldehyde fixing agent to change the hemoglobin content of the red blood cells, thereby changing their optical and electrical properties. In another example, human eosinophils are simulated using a hemoglobin denaturing solution to denature and precipitate the hemoglobin in red blood cells. U.S. Pat. No. 6,146,901 also describes to treat red blood cells with a mixed solution containing a polyhydric alcohol, a fixing agent and/or a non-ionic surfactant to obtain the desired white blood cell characteristics through changing the relative concentration of these components and their interaction time. These white blood cell analogs were finally mixed with soluble human red blood cells and stable platelets or platelet analogs to make up a multi-parameter whole blood control.

However, simulation of human white blood cells using animal red blood cells suffers from the disadvantage of limited simulation of individual characteristics of a certain type of white blood cell, as the animal red blood cells differ greatly from human white blood cells in morphology, membrane, cytoplasm granularity, nucleus and other inner structures. Moreover, where different types of five-part differential hematology analyzers vary in principles of detection, it is likely that a certain type of white blood cell particles simulated on a certain type of hematology analyzer might be represented as cell debris or other abnormalities on another type. Even though changing hemoglobin content and properties of red blood cells as described in the above-mentioned patents, it is not possible to completely simulate the various characteristics of different types of white blood cells. In particular, at the aspects of fluorescent binding, particle complexity and cell chemical staining etc., animal red blood cells hardly manifest the detection characteristics consistent with those of real white blood cells, which is a limitation to the application of the processing method. As for a five-part differential hematology analyzer, it is difficult and complicated to realize the simulation of five-part differential white blood cells using animal red blood cells, and compatibility is quite poor. Experimental results obtained by the present inventor also shows that white blood cell particles simulated by animal erythroblasts on a hematology analyzer based on the principle of multi-angle light scattering are too weak in cell clustering to obtain precise white blood cell differentiation. See the scattergram profiles in FIGS. 1 and 2. It can also be seen from the disclosed patents that animal red blood cells are not used for completely simulating human five-part differential white blood cells used in the quality control of five-part differential hematology analyzers.

Use of mammal white blood cells for preparation of five-part differential white blood cell analogs provides a better means to cope with complexity in reactions during the detection process of hematology analyzers varying in principles. On the whole, the methods in the prior art for treating white blood cells comprise the steps of hemolysis, fixation and washing, etc. For example, U.S. Pat. Nos. 6,406,915, 6,403,377, 6,399,388, 6,221,668, 6,200,500, 5,981,282, 5,731,205, 5,677,145, 5,672,474, 5,270,208, 5,262,327 describe to use the hemolytic agent Tris-ammonium chloride to completely lyse the red blood cells, and separate and then fix the human white blood cells. The white blood cell analogs were finally preserved in the preservation solution added with lipoprotein such that they approach the characteristics of real white blood cells. U.S. Pat. Nos. 6,762,055 and 6,514,763 also mainly concern the processes of removing red blood cells using mild chemical methods to retain intact white blood cells, then fixing the white blood cells through stepwise fixation to increase stability thereof, and finally obtaining white blood cell analogs. This patents place emphasis on the selective use of hemolytic agents and unique methods of fixation so that white blood cells could be preserved without addition of lipid substances such as cholesterol. In U.S. Pat. Nos. 6,187,590 and 5,858,790, the methods for preparing white blood cell analogs also involve lysing red blood cells and separating and then fixing white blood cells. The examples of U.S. Pat. No.

6,187,590 to Young also provides a method for preparing five-part differential white blood cell analogs using human white blood cells, with the basic procedures of hemolysis, fixation, washing and preservation as well. Furthermore, U.S. Pat. No. 6,759,246 describes a method of simulating human lymphocytes using porcine granulocytes. Neutrophils and eosinophils can also be simulated by porcine granulocytes, while monocyte analogs can be derived from bovine granulocytes.

The methods in the prior art for simulating human five-part differential white blood cells using mammal white blood cells all entails three basic steps of separating white blood cells through hemolysis, stabilizing or fixing them, and washing and preserving them. These methods suffer from the following disadvantages. The first disadvantage is represented by the complexity of hemolysis processes. For example, repeated use of hemolytic agents for the complete lysis of red blood cells or repeated washing after hemolysis to rinse away residual hemolytic agents are required before separating white blood cells for further fixation. As a matter of fact, during the process of lysing red blood cells completely, the light scattering properties of various types of white blood cells are liable to change, in particular the evident change occurring in scattering characteristics reflective of cell structure complexity of granulocytes. Also, repeated washing not only increases the probability of loss of white blood cells, but also further changes the light scattering property of white blood cells. See FIG. 4. Compared with FIG. 3, it can be seen that granulocytes have disappeared. As is mentioned in U.S. Pat. No. 5,270,208, the fresher whole blood is washed with isotonic salt solutions, its histogram changes over the wash times. Even if it is washed and fixed with solutions containing an aldehyde fixing agent, its histogram is still incorrect, and then addition of a lipoprotein protective agent is needed. The second disadvantage lies in long time of fixation. In order to increase the stability of white blood cells, the fixation time of the prior art is mostly over 2 hours. However, long-time action of the fixing agent will change the light scattering property of white blood cells to various degrees, e.g. increasing the intensity of high-angle light scattering of the cells. The third disadvantage derives from the addition of special components for the preservation solution. As mentioned in above referenced patents, a lipoprotein protective agent must be added in the cell preservation solution. Nonetheless, the addition of special components will increase the costs, and in addition, after whole blood control is formed, lipid substances would influence the stability of red blood cells contained therein and other components are necessary to be added in order to antagonize the side effects thereof.

SUMMARY OF THE INVENTION

The technical problem to be solved by the present invention is to obtain five-part differential white blood cells which perfectly retain the light scattering properties of every type of white blood cells, so that they have the same or similar characteristics for detection as various corresponding types of real white blood cells and also have much higher stability than that of real white blood cells. Thereby they can be used for the quality control of five-part differential hematology analyzers based on the principle of multi-angle light scattering.

Therefore, the present invention generally relates to a method for treating mammal white blood cells, with the main aims of simplifying the complex hemolytic process while retaining well the light scattering and other properties of various types of white blood cells so that they have the similar characteristics as fresh blood; and meanwhile, shortening the fixation time without influence on the stability of white blood cells for quality control; and with regard to preservation, eliminating the need for addition of lipid substances for better compatibility with other cell components.

It is therefore an objective of the present invention to provide a method for preparing a five-part differential white blood cell control, said method comprising the following steps of:

1) contacting concentrated blood cells with a hemolytic agent and/or an osmotic regulating agent;

2) adding a fixing agent to above mixed solution to conduct fast fixation;

3) regulating the concentration of the hemolytic agent and the fixing agent in above mixed solution with an isotonic solution;

4) adding the fixing agent to conduct reinforced fixation.

It is another objective of the present invention to provide a five-part differential white blood cell control prepared by the above-mentioned method.

It is yet another objective of the present invention to provide a whole blood control comprising the above-mentioned five-part differential white blood cell control.

It is a further objective of the present invention to provide a method for analyzing the white blood cells in the blood, comprising the steps of calibrating the hematology analyzer with the white blood cell control of the present invention before conducting analysis on the white blood cells of a blood sample.

It is still a further objective of the present invention to provide a method for analyzing blood, comprising the steps of calibrating the hematology analyzer with the white blood cell control of the present invention before conducting analysis on the white blood cells of a blood sample.

Other aspects and advantages of the present invention will become evident upon following drawings and description of particular examples.

DETAILED DESCRIPTION OF THE INVENTION

Figure 1:
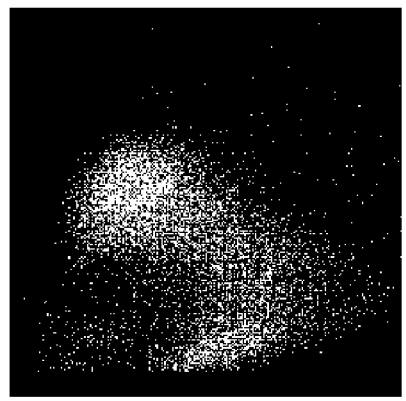
FIG. 1 is the scattergram profile of fixed avian red blood cells in the two white blood cell detection channels, i.e. white blood cell four-part differential DIFF channel and basophil BASO channel of a hematology analyzer based on the principle of multi-angle light scattering.
Figure 1:
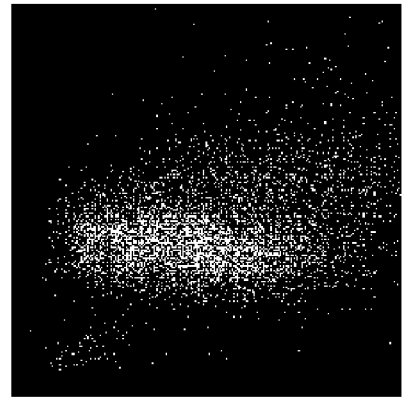
Figure 2:
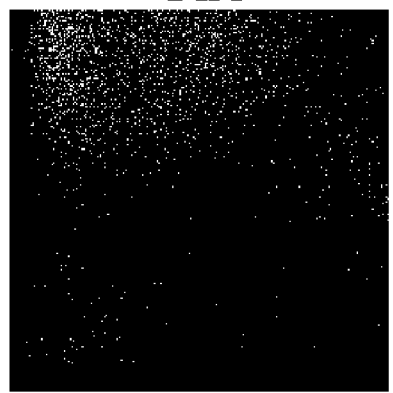
FIG. 2 is the scattergram profile of reptile red blood cells treated with two different methods in white blood cell four-part differential DIFF channel of a hematology analyzer based on the principle of multi-angle light scattering.
Figure 2:
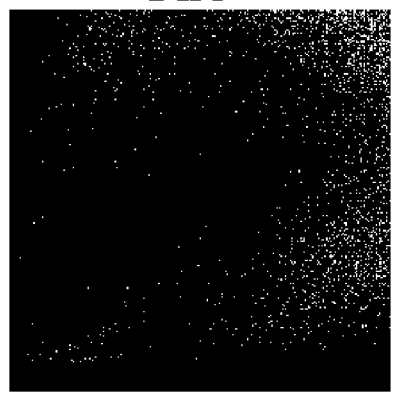

The term "five-part differential white blood cell(s)" as used herein refers to white blood cells comprising lymphocytes, monocytes, neutrophils, eosinophils and basophils. The five-part differential white blood cell analogs of the present invention are prepared from fresh human blood through a series of steps of treatment.

The term "DIFF" as used herein is short for "five-part differential" and refers to white blood cell five-part differential detection channel.

The term "hemolytic agent" as used herein includes any substance that can lyse the red blood cells in the blood, e.g. hemolytic agents having cationic, anionic, non-ionic or amphiprotic surfactants as active components, so long as they can achieve the objectives of the invention. In particular, the hemolytic agents of the present invention include conventional or commercially available hemolytic agents such as quaternary ammonium salts, saponins and ammonium chloride.

The term "osmotic regulating agent" as used herein includes any substance used for regulating osmotic pressure, e.g. phosphate salts, citrate salts, Tris-HCl or alkali metal salts. For example but without limitation, the osmotic pressure is in the range of 75-215 mOsm/Kg.

The term "fixing agent" as used herein includes any substance that can be used to fix cells, e.g. aldehyde compounds such as paraformaldehyde, formaldehyde, acetaldehyde, oxalaldehyde and glutaraldehyde or methanol, ethanol and acetone and the like, or the mixture thereof.

The term "washing solution" as used herein includes any solution that can be used to wash cells, e.g. conventional isotonic phosphate salt solution and sodium chloride solution.

The term "concentrated blood cells" as used herein refers to fresh healthy adult whole blood cells having higher concentration of white blood cells after concentrated through low temperature centrifugation, in which the concentration of white blood cells is about $4.0$–$35.0 \times 10^9$/L and that of red blood cells is about $1.0$-$6.0 \times 10^{12}$/L. The concentrated blood cells are stored at about 4° C. for use within 3 days. Prolonged storage will lead to evident change in the light scattering property of white blood cells, especially that of granulocytes.

In particular, one example of the present invention involves a method for preparing a five-part differential white blood cell control, said method comprising the following steps of:

1) contacting concentrated blood cells with a hemolytic agent and/or an osmotic regulating agent;
2) adding a fixing agent to above mixed solution to conduct fast fixation;
3) regulating the concentration of the hemolytic agent and the fixing agent in above mixed solution with an isotonic solution;
4) adding the fixing agent to conduct reinforced fixation.

In step 1), suitable hemolytic agents can be selected, e.g. solutions containing ammonium chloride or saponins, or commercially available hemolytic agents such as quaternary ammonium salts, to interact with fresh human concentrated blood cells in a certain volume ratio thereinto. As for mild hemolytic agents such as ammonium chloride, the amount for use can be increased or the action time can be extended. For example, the hemolytic agent and the concentrated blood cells can be in a volume ratio of about 3:1 to about 10:1, e.g. about 4:1, 6:1 or 8:1, and the action time of can range from about 3 to 10 minutes, e.g. 5, 6, 8 or 9 minutes. For intense hemolytic agents, the action time can be shortened and/or the amount used can be reduced. For example, the action time can range from about 30 seconds to about 3 minutes, e.g. about 40 seconds, 50 seconds, 1 or 2 minutes, and the hemolytic agent and the concentrated blood cells can be in a volume ratio of about 1:1 to about 8:1, e.g. about 2:1, 4:1 or 6:1. Meanwhile, osmotic regulating agents with a low osmotic pressure such as hypotonic salt solutions can be used concurrently to buffer the relatively intense hemolytic process, thereby optimizing the scattergram profile of white blood cells. Those skilled in the art may understand that the amount of a hemolytic agent to be used is well known in the art and can be adjusted depending on actual conditions by those skilled in the art. Besides, adjustments are also within the technical scope known to those skilled in the art.

In step 2), preliminary fixation is conducted. After fast hemolysis, an aldehyde fixing agent in suitable concentration is used to conduct fast fixation with the final concentration being, e.g. 0.001-5% and the action time 10-60 seconds. For example, a formaldehyde solution in final concentration of about 0.5-5% (e.g. about 1%, 2%, 3% or 4%) is used to act for about 10-60 seconds, e.g. about 20, 30, 40 or 50 minutes; or a glutaraldehyde solution in final concentration of about 0.001%-0.01% (e.g. 0.002% or 0.005%) is used to act for about 15-50 minutes, e.g. about 20, 30 or 40 minutes. Those skilled in the art may understand that the concentration and action time of an aldehyde fixing agent will be optimized depending on different hemolytic agents, aiming at avoiding partial fixation of red blood cells while stabilizing the light scattering property of white blood cells. Such optimization is within the technical scope known to those skilled in the art.

Figure 3:
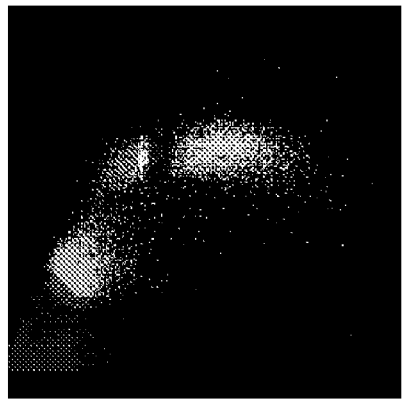
FIG. 3 is the scattergram profile of fresh human white blood cells in a hematology analyzer based on the principle of multi-angle light scattering.
Figure 3:
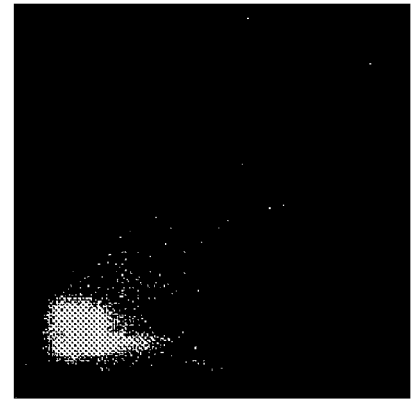
Figure 4:
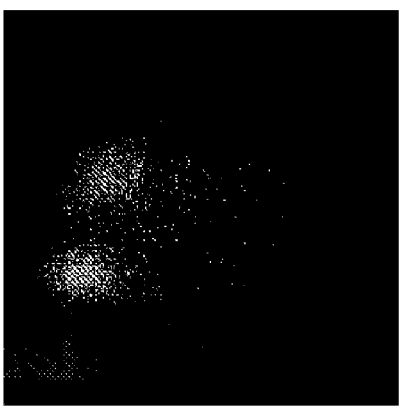
FIG. 4 is the scattergram profile of white blood cells from fresh human "concentrated blood cells" lysed by a hemolytic agent containing ammonium chloride and washed.
Figure 4:
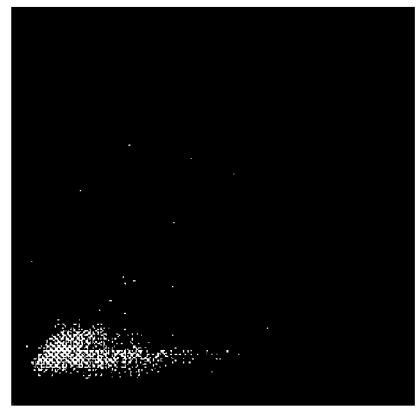
Figure 5:
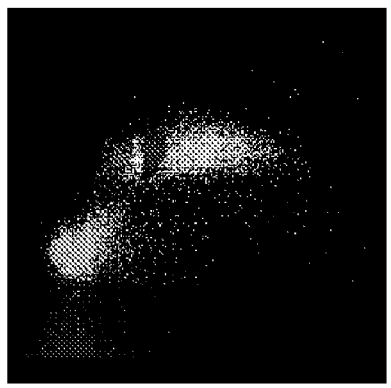
FIG. 5 is the scattergram profile of white blood cells after simultaneous hemolysis and fixation.
Figure 5:
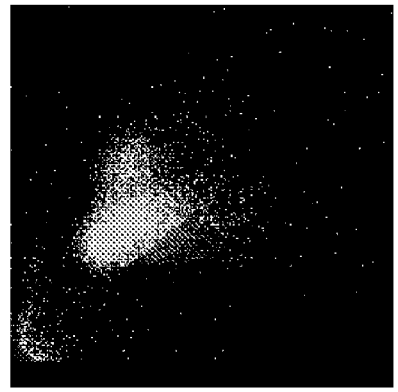

In step 3), hemolysis and fixation are processed simultaneously. The short-time hemolysis in step 1) usually fails to thoroughly lyse all red blood cells, and in particular, for concentrated blood cell material containing a significant amount of red blood cells, there may be more red blood cells residual. The residual red blood cells will ultimately interfere with the differential counting of lymphocytes. In order to completely lyse the red blood cells while maintaining the light scattering properties of various types of white blood cells, a suitable amount of an isotonic solution such as PBS, NaCl solution and the like is used to adjust the concentration of the hemolytic agent, the fixing agent and blood in above-mentioned mixed solution, for example, the volume ratio of the isotonic solution to the mixed solution being about 1:1 to about 5:1, e.g. about 2:1, 3:1 or 4:1. Then the mixture is incubated for about 5-60 minutes (e.g. about 10, 20, 30 or 50 minutes) to lyse the red blood cells thoroughly while well maintaining the structural characteristics of white blood cells. The incubation temperature is controlled at about 10° C.-30° C., for example, at 20° C. or room temperature. A higher temperature allows shortening the incubation time, otherwise, the incubation time is extended. Those skilled in the art may understand that the amount of fixing agent for use must be controlled in an appropriate range. A rather low concentration fails to maintain the light scattering property of white blood cells, while a rather high concentration will lead to partial fixation of red blood cells and change the light scattering property of white blood cells as well. Experiments (data not shown) indicated that a fixing agent in suitable concentration can even promote the disintegration of red blood cells. The reason for this is probably that a suitable amount of fixing agent weakens the flexibility of the membrane of red blood cells while strengthening the fragility, and the fixative effect of the fixing agent is worse than the hemolytic effect of the hemolytic agent, so that the membrane of red blood cells is more prone to break up in a hypotonic hemolytic environment. Moreover, the hemolytic agent may puncture the membrane of the white blood cells, which facilitates the fixing agent's entering into the cells that then has fixative effects on the inner structure of the cells. Those skilled in the art may also understand that white blood cells of different quality will be obtained by adjusting the conditions for action of the hemolytic agent. The extended action time, rising temperature, fortified concentration or increased action ratio of the hemolytic agent will firstly change the high-angle light scattering property of granulocytes, especially that of neutrophils, and then the low-angle light scattering property that is reflective of volume size, and gradually involves the change of light scattering property of monocytes. See FIGS. 4 and 5. Compared with FIG. 3, it can be seen that granulocytes that were only subjected to hemolysis disappeared from white blood cells, while white blood cells that were simultaneously subjected to hemolysis and fixation have a scattergram profile in the DIFF channel substantially consistent with that of real white blood cells.

Step 4) is a step for reinforced fixation. The life cycle of real blood cells is very short, especially that of granulocytes, for there are lysozymic components within the cytoplasmic particles which will lead to the autolysis of the cells after those particles are disintegrated. Therefore, it is necessary to sufficiently fix the white blood cells. In order to strengthen the stability of white blood cells and extend their storage period, on the basis of the semi-fixation (fast fixation), a reinforced fixation is further conducted using higher concentration of the fixing agent and/or different aldehyde fixing agents in a mixed ratio, with the final concentration of the fixing agent(s) being such as 0.05-8%. For example, formaldehyde in final concentration of about 4-8% (e.g. about 5%, 6% or 7%), or glutaraldehyde in final concentration of about 0.05-0.2% (e.g.0.1% or 0.15%), or a mixture thereof is used. The time for reinforced fixation can be controlled in the range of about 5-60 minutes, e.g. about 10, 30 or 45 minutes. The reaction temperature is controlled at about 10° C.-30° C, for example, at about 20° C. or room temperature. Those skilled in the art may understand that rising temperature allows an appropriate shortening of fixation time, otherwise, the fixation time can be appropriately extended. When conducting reinforced fixation, the concentration and action time of the fixing agent(s) must be controlled in a suitable range. Fixation in high concentration for a long time will not only strengthen the intensity of light scattering of white blood cells, but also increase the degree of aggregation of red blood cells, platelet debris and proteins, hence influencing the property of the final product. See FIG. 6 for the scattergram profile of cells after treatment. Compared with FIG. 3 and FIG. 5, it can be seen that the scattergram profile in the DIFF channel is substantially consistent with that of real white blood cells. However, in the BASO channel, it is shown that the white blood cells have had an obvious resistance against the hemolytic agent, with the scattergram profile distributing in the upper central position of the screen.

In another example of the invention, the present method further comprises steps of washing and preserving the fixed white blood cells. Following reinforced fixation, a preservation solution such as an isotonic solution is used to wash the white blood cells to rinse away the residual hemolytic agent, fixing agent as well as red blood cells and platelet debris, and the white blood cells are separated by centrifugation. After several repetition of washing and separation, the fixed five-part differential white blood cells are finally suspended in the preservation solution.

In accordance with above method of the present invention, a white blood cell control can be obtained which can well simulate the light scattering property of real white blood cells and hence be used in a five-part differential white blood cell hematology analyzer. Therefore, another example of the present invention provides a five-part differential white blood cell control prepared in accordance with the method of the present invention.

In a further example, the present invention provides a whole blood control comprising the white blood cell control of the present invention. The whole blood control is formed by combining the white blood cell control of the present invention with a red blood cell control and a platelet control in an appropriate ratio. Techniques for combining various components to form a whole blood control are well known in the art and are not detailed herein.

Those skilled in the art may understand that, without being bound by certain theories, it is generally believed that as the white blood cell control of the present invention is prepared using human white blood cells as raw materials, it shares similar properties with original human white blood cells and therefore can be used versatilely in various types of five-part differential white blood cell hematology analyzers based on the principle of multi-angle light scattering, for example, an all automatic hematology analyzer of Model BC-5500 (Mindray Bio-medical Electronics Co., Ltd, Shenzhen, P.R.C.). To this end, the various conditions in the steps described herein and the combination thereof can be adjusted depending on the particular instrument intended to be used, and such adjustment is well within the skill of the art.

In light of the above description, those skilled in the art will readily recognize the following advantages of the present invention. One advantage lies in the simplicity and versatility of the processing method. Avoided are the changes of optical characteristics of the white blood cells and the decrease in the yield due to repeated lysis of the red blood cells or repeated washing after hemolysis. The overall time for processing the white blood cells is short and therefore the cells have good stability. Moreover, the five-part differential white blood cells obtained by the method of the present invention retain the same characteristics as those of real white blood cells and have good compatibility with five-part differential hematology analyzers based on different principles. Optionally, through adjusting part of the steps or the ratio of the reagents, the present method can be also used for preparing five-part differential white blood cell controls that are adapted to different hematology analyzers. A second advantage lies in low cost. No special or expensive chemical reagents are needed during the processes of hemolysis, fixation, washing and preservation, which may avoid the occurrence of problems such as protein flocculation, cell aggregation and the need for addition of lipid substances as encountered in the techniques of the prior art.

In light of the description herein in combination with the common known prior art, those skilled in the art may understand that the white blood cell control of the present invention can be used in a method for blood diagnosis. Therefore, the present invention further provides a method for analyzing the white blood cells in the blood, said method comprising the steps of calibrating the hematology analyzer with the white blood cell control of the present invention before conducting analysis on the white blood cells of a blood sample.

Similarly, the present invention further provides a method for analyzing the blood, said method comprising the steps of calibrating the hematology analyzer with the white blood cell control of the present invention before conducting analysis on a blood sample.

EXAMPLE 1

One volume of concentrated blood cells is mixed with eight volume of hemolytic agent (10 mM $KHCO_3$, 155 mM $NH_4CL$, 0.01 mM $EDTA-Na_2.2H_2O$, 0.025% Saponin) for 5-minute fast reaction. Glutaraldehyde is then added in final concentration of 0.0065% for 20-second fast reaction. Afterwards, equal volume of isotonic solution (0.9% aqueous NaCl solution) is added and the mixture is incubated at room temperature for 50 minutes. Then to the reaction mixture is further added the mixed solution of formaldehyde and glutaraldehyde in final concentration of 6.5% and 0.05% respectively, Fixation continues for 40 minutes. Subsequently, the white blood cells are washed with isotonic salt solution (0.9% aqueous NaCl solution) for 3-5 times, each time the volume ratio of the white blood cell suspension to the washing solution being 1:5. The washed white blood cells are finally suspended in the isotonic salt solution (0.9% aqueous NaCl solution) and stored at 4° C.

EXAMPLE 2

One volume of concentrated blood cells is subjected to 2-minute fast reaction with four volume of commercial hemolytic agent LEOI (M-50LEO (I) hemolytic agent, Cat. No.: A12-000141, accompanying reagent for BC-5500) and hypotonic salt solution (in 1 L containing 1.764 g sodium citrate, 3.9 g NaCl, 0.084 g KCl, adjusted to pH 7.2 with 5% citric acid), and formaldehyde is then immediately added in final concentration of 4% for 40-second fast reaction. Afterwards, equal volume of isotonic solution (0.9% aqueous NaCl solution) is added and the mixture is further incubated at room temperature for 30 minutes. Then to the reaction mixture is added glutaraldehyde to final concentration of 0.1% and fixation continues 30 minutes. Subsequently, the white blood cells are washed with isotonic salt solution (0.9% aqueous NaCl solution) for 3-5 times, each time the volume ratio of the white blood cell suspension to the washing solution being 1:6. The washed white blood cells are finally suspended in the isotonic salt solution (0.9% aqueous NaCl solution) and stored at 4° C.

Figure 6:
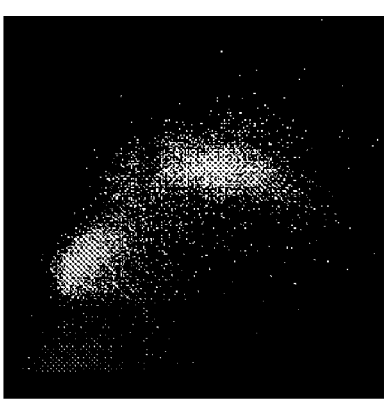
FIG. 6 is the scattergram profile of white blood cells after reinforced fixation.
Figure 6:
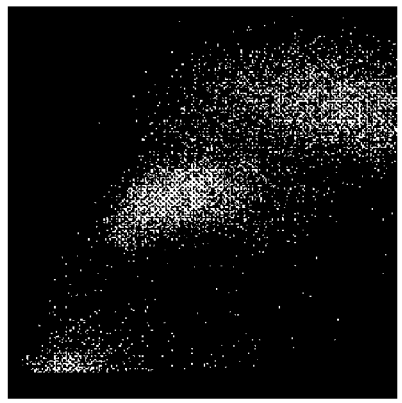

The finally obtained fixed white blood cells are subjected to white blood cell analysis on a hematology analyzer based on the principle of multi-angle light scattering, and the scattergram profile thereof is shown in FIG. 6. Compared with FIG. 3 and FIG. 5, it can be seen that the scattergram profile in the DIFF channel is still substantially consistent with that of real human white blood cells. However, in the BASO channel, it is shown that the white blood cells have had an obvious resistance against the hemolytic agent, with the scattergram profile distributing in the upper central position of the screen. It is obvious that the fixed white blood cells obtained by the method of the present method retain the light scattering properties of various types of white blood cells, and therefore can be used for the quality control of five-part differential hematology analyzers based on the principle of multi-angle light scattering.

All data, figures, instruments, reagents and steps herein shall be interpreted as illustrative but not limitative. Although the present invention has been described in reference to above particular examples, many modifications and other changes will occur to those skilled in the art. All such modifications and other changes are deemed to fall within the spirit and scope of the invention.

The invention claimed is:
1. A method for preparing a five-part differential white blood cell control, said method comprising the following steps of:
creating a mixed solution comprising concentrated whole blood cells, a hemolytic agent, a first amount of a first fixing agent, and an istonic solution, in which
the concentrated whole blood cells comprise red blood cells and white blood cells,
the isotonic solution is used at least for controlling a concentration of the concentrated whole blood cells, a concentration of the hemolytic agent, and a concentration of the first fixing agent, and the concentration of the first fixing agent is selected at least for preliminarily fixing the white blood cells without partially fixing at least some of the red blood cells to preserve a characteristic of the white blood cells, wherein the characteristic comprises a light scatting property, and
adding a second amount of the first fixing agent and/or an amount of a second fixing agent to the mixed solution in order to reinforce fixation of the white blood cells.
2. The method according to claim 1, further comprising washing to preserve the white blood cells which are fixed by at least the first fixing agent.
3. The method according to claim 2, wherein
the hemolytic agent comprises a mild hemolytic agent,
a volume ratio of the hemolytic agent to the concentrated whole blood cells comprises a range of 3:1 to 10:1, and
a reaction time for creating the mixed solution comprises a temporal range of 3 to 10 minutes.
4. The method according to claim 2, wherein
the hemolytic agent comprises an intense hemolytic agent,
a volume ratio of the hemolytic agent to the concentrated whole blood cells comprises a range of 1:1 to 8:1, and
a reaction time for creating the mixed solution comprises a temporal range of 30 seconds to 3 minutes with an optional addition of a low osmotic pressure agent to the mixed solution.
5. The method according to claim 2, wherein
the first fixing agent for preliminarily fixing the white blood cells without partially fixing at least some of the red blood cells comprises an aldehyde fixing agent with a fixing agent concentration of 0.001% to 5% and the first fixing agent preliminarily fixes the white blood cells for a reaction time comprising a range of 10 to 60 seconds.
6. The method according to claim 2, wherein
the isotonic solution comprises a PBS or NaCl solution,
a volume ratio of the isotonic solution to the mixed solution comprises a range of 1:1 to 1:5, and
an incubation time for the mixed solution comprises a temporal range of 5 to 60 minutes at a temperature comprising a temperature range of 10 to 30° C.
7. The method according to claim 2, wherein
the act of adding the second amount of the first fixing agent and/or the amount of the second fixing agent comprises adding an aldehyde fixing agent with a fixing agent concentration comprising a range of 0.05% to 8% for a reaction time comprising a temporal range of 5 to 60 seconds at a reaction temperature comprising a temperature range of 10 to 30° C.
8. The method according to claim 7, wherein the act of adding the second amount of the first fixing agent and/or the amount of the second fixing agent comprises adding a formaldehyde solution with a formaldehyde concentration of 4% to 8% or a glutaraldehyde solution with a glutaraldehyde concentration of 0.05% to 0.2% or a mixture of the formaldehyde solution and the glutaraldehyde solution.
9. The method according to claim 1, wherein
the hemolytic agent comprises a mild hemolytic agent,
a volume ratio of the hemolytic agent to the concentrated whole blood cells comprises a range of 3:1 to 10:1, and
a reaction time for creating the mixed solution comprises a temporal range of 3 to 10 minutes.
10. The method according to claim 1, wherein
the hemolytic agent comprises an intense hemolytic agent,
a volume ratio of the hemolytic agent to the concentrated whole blood cells comprises a range of 1:1 to 8:1, and a reaction time for creating the mixed solution comprises a temporal range of 30 seconds to 3 minutes with an optional addition of a low osmotic pressure agent to the mixed solution.

11. The method according to claim 1, wherein
the first fixing agent for preliminarily fixing the white blood cells without partially fixing at least some of the red blood cells comprises an aldehyde fixing agent with a fixing agent concentration of 0.001% to 5% and the first fixing agent preliminarily fixes the white blood cells for a reaction time comprising a range of 10 to 60 seconds.

12. The method according to claim 1, wherein
the isotonic solution comprises a PBS or NaCl solution,
a volume ratio of the isotonic solution to remaining mixed solution comprises a range of 1:1 to 1:5, and
an incubation time for the mixed solution comprises a temporal range of 5 to 60 minutes at a temperature comprising a temperature range of 10 to 30° C.

13. The method according to claim 1, wherein
the act of adding the second amount of the first fixing agent and/or the amount of the second fixing agent comprises adding an aldehyde fixing agent with a fixing agent concentration comprising a concentration range of 0.05% to 8% for a reaction time comprising a temporal range of 5 to 60 seconds at a reaction temperature comprising a temperature range of 10 to 30° C.

14. The method according to claim 13, wherein the act of adding the second amount of the first fixing agent and/or the amount of the second fixing agent comprises:
adding a formaldehyde solution with a formaldehyde concentration of 4% to 8% or a glutaraldehyde solution with a glutaraldehyde concentration of 0.05% to 0.2% or a mixture of the formaldehyde solution and the glutaraldehyde solution.

15. The method of claim 1, further comprising:
adding an osmotic regulating agent to the mixed solution to buffer a process of dissolving the red blood cells.

16. The method of claim 1, in which the first fixing agent facilitates a hemolytic process of at least some of the red blood cells.

* * * * *